United States Patent [19]

Tabor et al.

[11] Patent Number: 5,534,407
[45] Date of Patent: Jul. 9, 1996

[54] METHOD FOR NUCLEIC ACID HYBRIDIZATION USING SINGLE-STRANDED DNA BINDING PROTEIN

[75] Inventors: Stanley Tabor, Cambridge; Charles C. Richardson, Chestnut Hill, both of Mass.

[73] Assignee: President and Fellows of Harvard College, Cambridge, Mass.

[21] Appl. No.: 229,396

[22] Filed: Apr. 18, 1994

Related U.S. Application Data

[63] Continuation of Ser. No. 826,955, Jan. 28, 1992, abandoned.
[51] Int. Cl.$^6$ .............................. C12Q 1/70; C12Q 1/68
[52] U.S. Cl. .................................. 435/5; 435/6; 935/77; 935/78
[58] Field of Search .......................... 435/6, 5; 935/77, 935/78

[56] References Cited

U.S. PATENT DOCUMENTS 5,015,569   5/1991   Pontius ................................ 435/6

FOREIGN PATENT DOCUMENTS 8505685   12/1985   WIPO ................................ 435/6
9006219   10/1990   WIPO .

OTHER PUBLICATIONS

Alberts et al., Nature 227:1313–1318 (Sep. 26, 1970).
Christiansen et al. J. Mol. Biol. 115:441–454 (1977).
Rueben et al. PNAS.USA 70(6):1846–1850 (Jun. 1973).
Alberts and Frey, "T4 Bacteriophage Gene 32: A Structural Protein in the Replication and Recombination of DNA", 227 *Nature* 1313, 1970.
Christiansen and Baldwin, "Catalysis of DNA Reassociation by the *Escherichia coli* DNA Binding Protein", 115 *J. Mol. Biol.* 441, 1977.
Weinstock et al., "ATP–dependent Renaturation of DNA Catalyzed by the RecA Protein of *Escherichia coli*", 76 *Proc. Natl. Acad. Sci. USA* 126, 1979.
McEntee, "Kinetics of DNA Renaturation Catalyzed by the RecA Protein of *Escherichia coli*", 24 *Biochem.* 4345, 1985.
Bryant and Lehman, "On the Mechanism of Renaturation of Complementary DNA Strands by the RecA Protein of *Escherichia coli*", 82 *Proc. Natl. Acad. Sci. USA* 297, 1985.
Araki and Ogawa, "The Participation of T7 DNA–Binding Protein in T7 Genetic Recombination", 111 *Virology* 509, 1981.
Dunn and Studier, "Nucleotide Sequence From the Genetic Left End of Bacteriophage T7 DNA to the Beginning of Gene 4", 148 *J. Mol. Biol.* 303, 1981.
Argos et al., "Primary Structural Relationships May Reflect Similar DNA Replication Strategies, 149 *Virology* 208, 1986.
Scherzinger et al., "Stimulation of T7 DNA Polymerase by a New Phage–Coded Protein" 123 *Mol. General Genetics* 247, 1973.

Reuben and Gefter, "A DNA–Binding Protein Induced by Bacteriophage T7", 70 *Proc. Natl. Acad. Sci. USA* 1846, 1973.
Reuben and Gefter, "A Deoxyribonucleic Acid–Binding Protein Induced by Bacteriophage T7", 249 *J. Biol. Chem.* 3843, 1974.
Nakai and Richardson, "The Effect of the T7 and *Escherichia coli* DNA–Binding Proteins at the Replication Fork of Bacteriophage T7", 263 *J. Biol. Chem.* 9831, 1988.
Fuller and Richardson, "Initiation of DNA Replication at the Primary Origin of Bacteriophage T7 by Purified Proteins", 260 *J. Biol. Chem.* 3197, 1985.
Mendelman and Richardson, "Requirements for Primer Synthesis by Bacteriophage T7 63–kDa Gene 4 Protein", 266 *J. Biol. Chem.* 23240, 1991.
Scherzinger and Klotz, "Studies on Bacteriophage T7 DNA Synthesis *in vitro*", 141 *Molec. Gen. Genetics* 233, 1975.
Araki and Ogawa, "A T7 Amber Mutant Defective in DNA–Binding Protein", 183 *Molec. Gen. Genetics* 66, 1981.
Araki and Ogawa, "Novel Amber Mutants of Bacteriophage T7, Growth of Which Depends on *Escherichia coli* DNA–Binding Protein", 118 *Virology* 260, 1982.
Muniyappa and Radding, "The Homologous Recombination System of Phage λ", 261 *J. Biol. Chem.* 7472, 1986.
Kmice and Holloman, "β Protein of Bacteriophage λPromotes Renaturation of DNA", 266 *J. Biol. Chem.* 12636, 1981.
Halbrook and McEntee, "Purification and Characterization of a DNA–pairing and Strand Transfer Activity from Mitotic *Saccharomyces cerevisiae*", 264 *J. Biol. Chem.* 21403, 1989.
Tabor et al., "*Excherichia coli* Thioredoxin Confers Processivity on the DNA Polymerase Activity of the Gene 5 Protein of Bacteriophage T7", 262 *J. Biol. Chem.* 16212, 1987.
Tabor and Richardson, "DNA Sequence Analysis With a Modified Bacteriophage T7 DNA Polymerase", 84 *Proc. Natl. Acad. Sci. USA* 4767, 1987.
Tabor and Richardson, "Selective Inactivation of the Exonuclease Activity of Bacteriophage T7 DNA Polymerase by *in vitro* Mutagenesis", 264 *J. Biol. Chem.* 6447, 1989.

(List continued on next page.)

Primary Examiner—Stephanie W. Zitomer
Attorney, Agent, or Firm—Lyon & Lyon

[57] ABSTRACT

Method of nucleic acid hybridization for detecting the presence of a specific nucleic acid sequence in a population of different nucleic acid sequences using a nucleic acid probe. The nucleic acid probe hybridizes with the specific nucleic acid sequence but not with other nucleic acid sequences in the population. The method includes contacting a sample (potentially including the nucleic acid sequence) with the nucleic acid probe under hybridizing conditions in the presence of a single-stranded DNA binding protein provided in an amount which stimulates renaturation of a dilute solution (i.e., one in which the $t_{1/2}$ of renaturation is longer than 3 weeks) of single-stranded DNA greater than 500 fold (i.e., to a $t_{1/2}$ less than 60 min, preferably less than 5 min, and most preferably about 1 min.) in the absence of nucleotide triphosphates.

6 Claims, 2 Drawing Sheets

OTHER PUBLICATIONS

Sadowski et al., "Genetic Recombination of Bacteriophage T7 DNA *in vitro*", 19 *ICN–UCLA Symposia on Mol. and Cell. Biol.* 941, 1980.

White, abstract, "Formation and Processing of Concatemers of Bacteriophage T7 DNA, *In Vitro*", 1986.

White, PhD Thesis, "Formation and Processing of Concatemers of Bacteriophage T7 DNA *In Vitro*", 1986 pp. 9–13, 64, 67, 71, 74, 75, 82, 85.

Pontius, U.S. Pat. No. 5,015,569, issued May 14, 1991.

Nielson and Mathur, International Application No. WO91/06679 May 16, 1991.

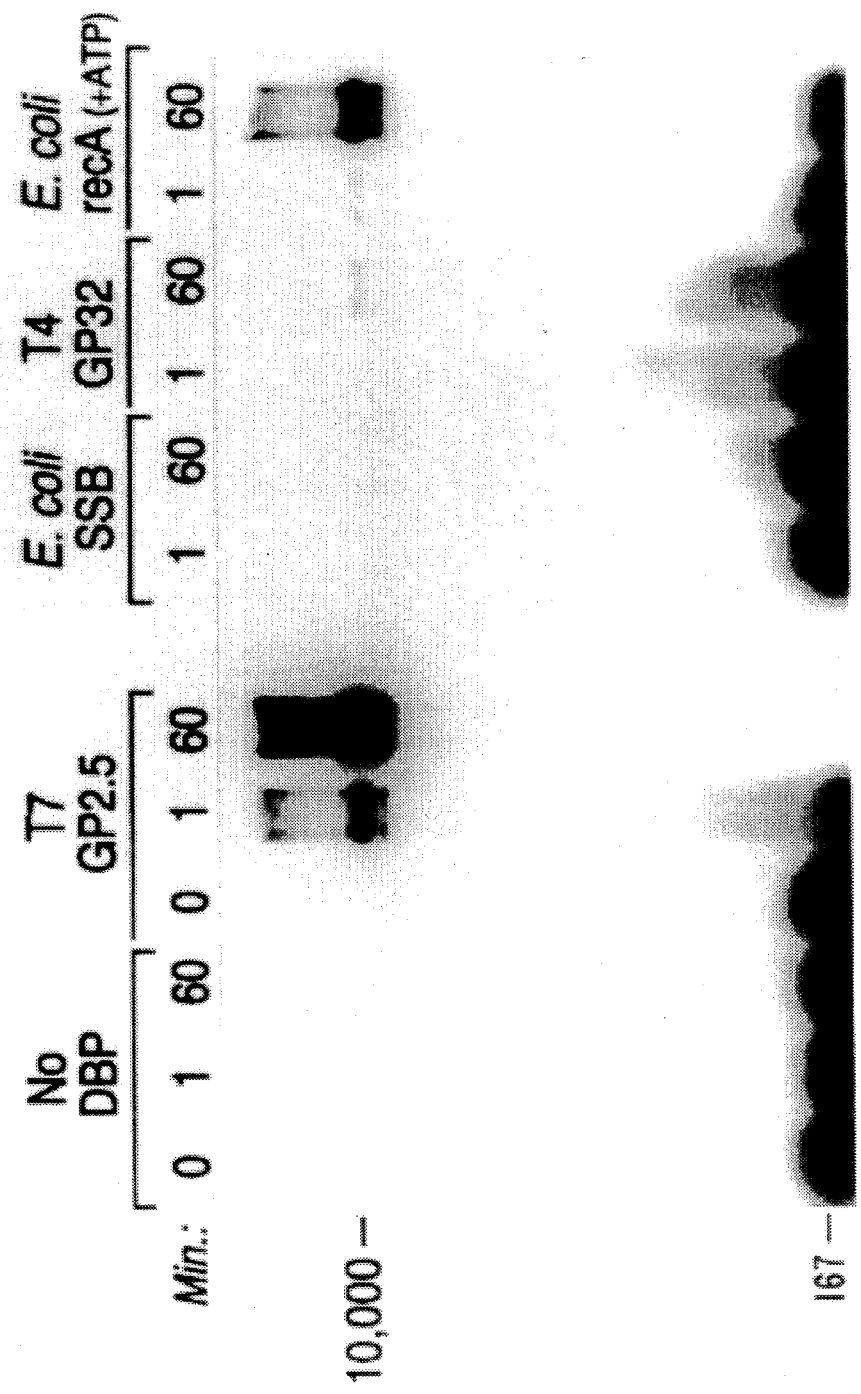

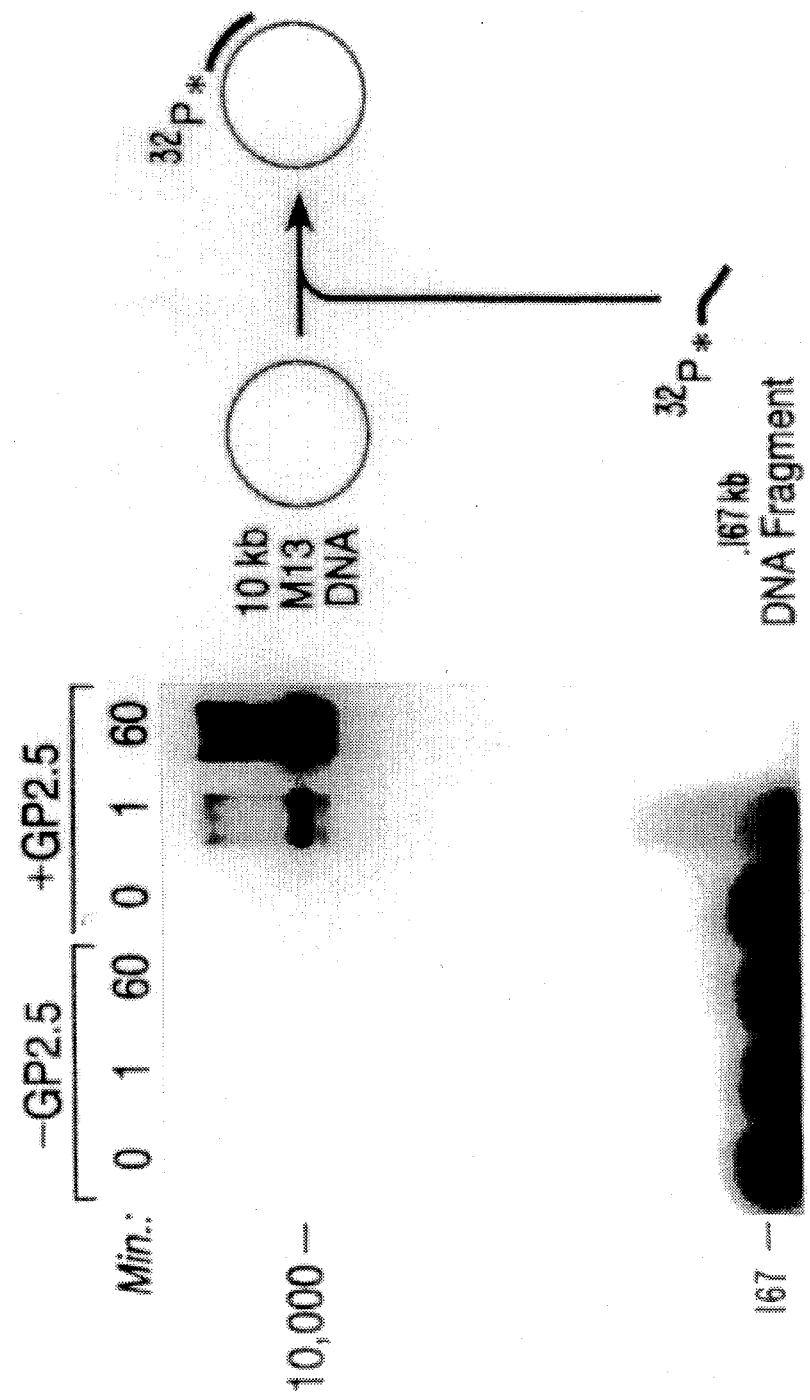

5,534,407

METHOD FOR NUCLEIC ACID HYBRIDIZATION USING SINGLE-STRANDED DNA BINDING PROTEIN

This invention was supported under DOE Grant No. DE-GF02-88ER60688, and the U.S. Government has certain rights to the invention.

This application is a continuation of application Ser. No.07/836,955, filed Jan. 28, 1992, now abandoned

BACKGROUND OF THE INVENTION

This invention relates to methods for nucleic acid hybridization, and in particular hybridization performed at low nucleic acid concentrations.

Nucleic acid binding proteins, and in particular, single-stranded DNA binding proteins have been identified in a number of biological systems. Some such proteins play a role in renaturation of DNA. For example, Alberts and Frey, 227 *Nature* 1313, 1970, describe renaturation of purified DNA by the T4 bacteriophage gene 32 protein and propose that it accelerates renaturation by "forcing DNA single strands into an unfolded conformation which leaves their bases available for pairing during chance collisions between complementary strands." Christiansen and Baldwin, 115 *J. Mol. Biol.* 441, 1977, describe reassociation of DNA in the presence of a DNA binding protein from *E. coli*. They note that spermidine and putrescine together also increase the rate of reassociation of DNA. Weinstock et al., 76 *Proc. Natl. Acad. Sci. USA* 126, 1979, McEntee, 24 *Biochem.* 4345, 1985, and Brian and Lehman, 82 *Proc. Natl. Acad. Sci. USA* 297, 1985, describe DNA renaturation in the presence of recA protein, and its stimulation by ATP and magnesium ions.

Araki and Ogawa, 111 *Virology* 509, 1981, describe a T7 phage-encoded factor which facilitates binding of nicked open circular ColE1 DNA to cellulose bound ColE1 DNA in the presence of a T7 5'-exonuclease.

Dunn and Studier, 148 *J. Mol. Biol.* 303, 1981, describe the nucleotide sequence of bacteriophage T7 DNA including a sequence encoding the gene 2.5 protein, which is identified as a single-stranded DNA binding protein. The sequence of this single-stranded DNA binding protein is compared to that from *E. coli* by Argoss et al., 149 *Virology* 208, 1986. Significant homology between the two proteins exists.

Scherzinger et al., 123 *Mol. General Genetics* 247, 1973, Reuben and Gefter, 70 *Proc. Natl. Acad. Sci. USA* 1846, 1973, and Reuben and Gefter 249 *J. Biol. Chem.* 3843, 1974, Nakai and Richardson, 263 *J. Biol. Chem.* 9831, 1988, Fuller and Richardson, 260 *J. Biol. Chem.* 3197, 1985, Mendelman and Richardson, 266 *J. Biol. Chem.* 23, 240, 1991, Scherzinger and Klotz, 141 *Molec. Gen. Genetics* 233, 1975, Araki and Ogawa, 183 *Molec. Gen. Genetics* 66, 1981, and Araki and Ogawa, 118 *Virology* 260, 1982 describe properties of gene 2.5 protein. It is identified as having a molecular weight of about 25,000 to 31,000 and as having single-stranded DNA binding properties. It also stimulates DNA synthesis by T7 DNA polymerase on single-stranded templates.

SUMMARY OF THE INVENTION

The invention features an improved method of nucleic acid hybridization, for detection of a specific nucleic acid sequence, by use of a single-stranded DNA binding protein that promotes hybridization of single-stranded (ss) nucleic acid (generally RNA or DNA) fragments in solution. Such a protein also promotes hybridization when one fragment to be hybridized is bound to a solid support. In particular, the single-stranded DNA binding protein stimulates renaturation of dilute solutions of single-stranded DNA greater then 500 fold even in the absence of nucleoside triphosphates (e.g., ATP) and preferably even in the absence of magnesium ions. For example, such dilute solutions of nucleic acids have a half-life of hybridization ($t_{1/2}$) in the absence of single-stranded DNA binding protein of greater than 3 weeks (as defined below). This half life is reduced to less than about 1 minute in the presence of a single-stranded DNA binding protein useful in this invention.

An example of such a useful single-stranded DNA binding protein is the gene 2.5 protein of bacteriophage T7, and equivalent such T7-type phage proteins or other proteins. Examples of T7-type phages include T7, T3,φI, ΦII, H, W31, gh-1, Y, A1122 and SP6. These single-stranded binding proteins significantly enhance renaturation of DNA even under physiological conditions such as at 37° C., pH 7.5, at dilute nucleic acid concentrations without the need for ATP even in physiological samples, such as sputum, blood, urine, and faeces.

Those single-stranded DNA binding proteins which are useful in the invention are readily identified by the specific assay method described below. In this assay, a suitable protein for use in the method of this invention will stimulate hybridization of a 167-mer at 2.2 ng/ml (i.e., about 6.7 nM nucleotide, 1 fmole fragment) with single-stranded M13 DNA at template 130 ng/ml (i.e., about 400 nM nucleotide, 1 fmole fragment) by greater than 500 fold in the absence of nucleoside triphosphates. Indeed, the renaturation rate is stimulated at least 5,000 fold in preferred embodiments.

Such stimulation may require the presence of sodium chloride. The concentration of sodium chloride necessary depends on the amount of magnesium ions present in the mixture. For example, in the absence of magnesium ions, the optimum sodium chloride concentration is about 150 mM, while in the presence of 10 mM magnesium chloride the optimum sodium chloride concentration is 50 mM.

Examples of proteins which might be tested include those described by Muniyappa and Radding, 261 *J. Biol. Chem.* 7472, 1986, and Kmiec and Holloman, 266 *J. Biol. Chem.* 12, 636, 1981, namely, phage lambda β-protein, and Halbrook and McEntee, 264 *J. Biol. Chem.* 21, 403, 1989, namely, DNA pairing protein. Neither of these proteins require ATP or other nucleotides and thus are useful in the invention.

Thus, the invention features a method (and kits useful in such a method) of nucleic acid hybridization for detecting the presence of a specific nucleic acid sequence in a population of different nucleic acid sequences using a nucleic acid probe specific for the sequence to be detected. That is, the nucleic acid probe hybridizes with the specific nucleic acid sequence but not with other nucleic acid sequences in the population. The method includes contacting a sample (potentially including the nucleic acid sequence) with the nucleic acid probe under hybridizing conditions in the presence of a single-stranded DNA binding protein provided in an amount which stimulates renaturation of a dilute solution (i.e., one in which the t2 $_{1}$/2 renaturation is longer than 3 weeks) of single-stranded DNA greater than 500 fold (i.e., to a $t_{1/2}$ less than 60 min, preferably less than 5 min, and most preferably less than about 1 min.) in the absence of nucleoside triphosphates. One example of such a dilute solution is provided below where about 1 fmole ss DNA fragments are used in the method. Of course, the nucleic acid being hybridized need not be present in only dilute amounts, but the method of this invention is effective even at such concentrations.

In preferred embodiments, the nucleic acid molecules include heterologous nucleic acid, that is, the nucleic acid present in the sample is derived from more than one type of organism, e.g., a bacterium and a virus, or a virus and a mammal as is common in physiological samples. In addition, the single-stranded binding protein is a T7-type phage-derived protein, e.g., a gene 2.5 type protein produced by recombinant DNA technology. In more preferred embodiments, the method is a solution phase hybridization, or a Southern or a northern blot.

Other features and advantages of the invention will be apparent from the following description of the preferred embodiments thereof, and from the claims.

DESCRIPTION OF THE PREFERRED EMBODIMENTS

The drawings will first briefly be described.
Drawings FIG. 1 is a reproduction of an autoradiogram showing stimulation of renaturation by gene 2.5 protein
FIG. 2 is a reproduction of an autoradiogram comparing renaturation rates with various single-stranded DNA binding proteins and a diagrammatic representation of the test system used (right hand side);

Binding Proteins

Single-stranded DNA binding proteins useful in the invention are generally described above. Useful such proteins can be identified as described below by simply substituting a chosen single-stranded DNA binding protein for the gene 2.5 protein or the other single-stranded DNA binding proteins used in the example below. Given that applicant has recognized that single-stranded DNA binding proteins which do not require ATP or other nucleotides are useful for enhancing hybridization reactions, those of ordinary skill in the art will recognize that many known single-stranded DNA binding proteins should be tested in the assay described below (or its equivalent) to identify whether they too are useful in the hybridization method of this invention.

It is preferred that a recombinant single-stranded DNA binding protein be used in the hybridization method of this invention. Recombinant protein can be produced in greater quantity, and with greater purity than its equivalent naturally occurring protein isolated, for example, from phage infected cells. An example of a method to purify the T7 gene 2.5 protein is provided below to illustrate production of such recombinant proteins.

Purification of the T7 Gene 2.5 Protein

Several procedures have been described for the purification of single-stranded DNA binding proteins. The purification scheme described here is a modification of these procedures. The purification of gene 2.5 protein from 20 g of cells is summarized in Table I.

TABLE I

Purification of T7 gene 2.5 protein from 20 g of induced
E. coli BL21 (DE3) containing the plasmid pAR511-2.5

| Fraction | Step | Protein mg | Total units[a] | Specific activity units/mg protein |
|---|---|---|---|---|
| I | Extract | 1,770 | ND[b] | |
| II | DEAE-cellulose | 1,426 | ND[b] | |
| III | Ammonium sulfate | 986 | ND[b] | |
| IV | Sephacryl S-200 | 760 | 24,500 | 32 |
| V | Single-stranded DNA-cellulose | 48 | 6,672 | 139 |
| VI | DEAE-Sephacel | 36 | 5,724 | 159 |
| VII | Mono Q | 34 | 5,472 | 160 |

[a]One unit is equal to one nmol of nucleotides of M13 DNA bound as determined by the nitrocellulose filter binding assay described under "Experimental Procedures."
[b]Not determined. The number of units of gene 2.5 protein could not be determined in these fractions due to the presence of contaminating single-stranded DNA binding proteins.

Gene 2.5 protein was monitored both by it binding to single-stranded M13 [$^3$H]DNA using a nitrocellulose filter binding assay described by Whitter and Chase, 106 *Anal. Biochem.* 99, 1980, and standard SDS-PAGE analysis. All purification steps were carried out at 0°–4° C. unless otherwise indicated.

Overproduction of Gene 2.5 Protein

The plasmid pAR511-2.5 (obtained from Dr. Studier, Brookhaven, Nat'l Lab., Upton, NY) contains gene 2.5 under the control of T7 RNA polymerase. Gene 2.5 was overexpressed by induction of T7 RNA polymerase in the strain *E. coli* BL21(DE3) (Studier and Moffatt, 189 *J. Mol. Biol.* 113, 1986). *E. coli* BL21(DE3) containing pAR511-2.5 was grown overnight in 500 ml of 1% tryptone, 0.5% yeast extract, 1% NaCl,0.1% casamino acids, 20 mM KPO$_4$, pH 7.4, and 50 µg/ml ampicillin. This culture was used to inoculate 10 liters of 2% tryptone, 1% yeast extract, 0.5% NaCl, 0.2% casamino acids, 40 mM KPO$_4$, pH 7.4 , and 50 µg/ml ampicillin in a New Brunswick fermenter. The cells were incubated with aeration at 37° C. At a cell density corresponding to A$_{590}$=4.5,isopropyl-β-D-thiogalactopyranoside (IPTG) was added at a final concentration of 0.4 mM to induce the expression of T7 RNA polymerase, and thus gene 2.5 protein. After induction, the cells were incubated for three additional hours and then harvested by centrifugation at 6,000× g for 10 min in a Sorvall GS-3 rotor. The cell paste was resuspended in 2.5 liters 50 mM Tris-HCl , pH 7.5, 25 mM EDTA, and 10% sucrose, and again harvested by centrifugation. The cell paste (88 g) was resuspended in 400 ml 50 mM Tris-HCl, pH 7.5, 1 mM EDTA, and 10% sucrose, and 90 ml aliquots (20 g of cells) were frozen in liquid N$_2$ and stored at −80°C.

Preparation of Cell Extract

Frozen cells (20 g in 90 ml) were thawed overnight on ice. Two ml lysozyme (10 mg/ml) and 11 ml 50 mM Tris-HCl, pH 7.51, 1 mM EDTA, 10% sucrose, 1M NaCl, 100 mM bezamidine chloride, and 5 mM phenylmethylsulfonyl fluoride were added. After incubation of the mixture for 45 min on ice with intermittent stirring, 24 ml 50 mM Tris-HCl, pH 7.51 , mM EDTA, 5M NaCl was added to bring the final concentration of NaCl to 1M. The cells were heated in a 37°

C. water bath with constant stirring until the temperature reached 20° C. and then cooled in an ice-water bath until the temperature was reduced to 4° C. The lysate was centrifuged for 45 min at 40,000 rpm in a Beckman Ti-45 rotor. The supernatant (120 ml) was Fraction I.

DEAE-cellulose Chromatography

A column of Whatman DE52 DEAE-cellulose (5.8 cm$^2$× 30 cm) was prepared and equilibrated with 20 mM Tris-HCl, pH 7.5, 1 mM EDTA, 0.1 mM DTT, and 10% glycerol (Buffer A) containing 0.4M NaCl . Fraction I was diluted with Buffer A to give a conductivity equivalent to Buffer A containing 0.4M NaCl . The diluted Fraction I (~300 ml) was applied to the column. Gene 2.5 protein is not retained under these conditions. The flow-through fractions (~300 ml) were pooled to give Fraction II.

Ammonium Sulfate Precipitation

To 300 ml of fraction II, ammonium sulfate was added to 80% saturation (155 g) over a period of 60 min, and was stirred slowly for an additional 60 min. The precipitate was collected by centrifugation at 10,000× g for 45 min in a Sorvall GSA rotor, and dissolved in 50 ml of Buffer A containing 50 mM NaCl (Fraction III).

Sephacryl S-200 Chromatography

A column of Sephacryl S-200 (3.8 cm$^2$×60 cm) was prepared and equilibrated with Buffer A containing 50 mM NaCl. From this point on gene 2.5 protein was monitored by absorbance at 280 nm, SDS-PAGE, and its ability to bind single-stranded DNA using the nitrocellulose filter binding assay. Fractions (32 ml) containing single-stranded DNA binding activity were pooled (Fraction IV).

Single-stranded DNA-cellulose Chromatography

A column of single-stranded DNA-cellulose (2.5 cm$^2$×12 cm) containing approximately 5 g of single-stranded DNA-cellulose (5.4 mg of denatured salmon sperm DNA per g of cellulose) was prepared by the procedure of Alberts and Herrick (21 *Meth. Enz.* 198, 1971). The column was equilibrated with Buffer A containing 50 mM NaCl. Fraction IV was applied to the column at a rate of 48 ml/h. Gene 2.5 protein was eluted by a step gradient containing increasing NaCl concentrations, with each step (100) containing Buffer A plus either 0.1M, 0.5M, 1.0M, or 2.0M NaCl. One ml fractions were collected. Most of the gene 2.5 protein eluted in 30 ml of Buffer A plus 1.0M NaCl (Fraction V).

DEAE-Sephacel Chromatography

A column of DEAE-Sephacel (2.5 cm$^2$ ×28 cm) was prepared and equilibrated with Buffer A containing 0.1M NaCl. Fraction V was dialyzed against Buffer A to reduce the conductivity to that of Buffer A containing 0.1M NaCl. The dialyzed fraction V was applied to the column at a flow rate of 23 ml/h, and the resin was washed with 150 ml of Buffer A containing 0.1M NaCl. Gene 2.5 protein was eluted with a 300 ml linear gradient from 0.1M to 0.5M NaCl in Buffer A at a flow rate of 23 ml/h. One ml fractions were collected. Gene 2.5 protein eluted at approximately 0.25M NaCl. The fractions (15 ml) containing gene 2.5 protein were pooled and analyzed by SDS-PAGE (Fraction VI). Fraction VI appears to be homogenous as a single band judged by electrophoresis under the denaturing conditions, but it contains a low level of single-stranded DNA dependent nucleoside 5'-triphosphatase activity.

Mono Q FPLC

To remove a contaminating single-stranded DNA dependent nucleoside triphosphatase in Fraction VI, several portions of Fraction VI were dialyzed against Buffer A and were chromatographed separately on the Mono Q column equilibrated in Buffer A. In each run, the column was washed with 10 ml of Buffer A, ad eluted with a 45-ml gradient of Buffer A containing 0–600 mM NaCl. Single-stranded DNA dependent ATPase was assayed across the column. The DNA dependent ATPase activity eluted from the column slightly before the bulk of the gene 2.5 protein. Fractions of gene 2.5 protein showing no ATPase were pooled, dialyzed against 20 mM KPO$_4$, pH 7.4, 0.1 mM DTT, 0.1 mM EDTA, and 50% glycerol at 4° C., and stored at −20° C. (Fraction VII).

Purity of Gene 2.5 Protein 36 mg of gene 2.5 protein were recovered from 20 g of induced cells. After electrophoresis of the purified gene 2.5 protein under denaturing conditions, staining with Coomassie Blue produced a single band corresponding to a molecular weight of approximately 27,000. Although the gene 2.5 protein present in Fraction VI appears homogeneous, a low level of single-stranded DNA dependent nucleoside 5'-triphosphatase activity (5 molecules of ATP hydrolyzed to ADP and Pi per min per monomer of gene 2.5 protein) is present in the fraction. FPLC chromatography of the gene 2.5 protein Fraction VI on a Mono Q column as described above separated the ATPase from the gene 2.5 protein. Fraction VII of gene 2.5 protein has no detected nucleoside 5'-triphosphatase activity (less than 0.1 molecule of ATP hydrolyzed per min per monomer of gene 2.5 protein). The contaminating ATPase present in Fraction VI represents less than 1% of the protein in this fraction.

EXAMPLE 1

Assay for Renaturation of Single-Stranded DNA

Referring to FIGS. 1–2, the results of renaturation experiments are provided. These experiments were performed generally as described below or as shown in the diagrams associated with FIG. 1. These data demonstrate highly efficient renaturation in the presence of gene 2.5 protein compared to that in the absence of any single-stranded DNA binding protein, or in the presence of T4 gene 32 protein, *E. coli* SSB protein, and *rec*A protein (even in the presence of ATP).

The annealing of a $^{32}$P-labeled 167 nucleotide single-stranded DNA fragment to an ~10,000 nucleotide circular M13 single-stranded DNA molecule was measured by agarose gel electrophoresis.

The M13 DNA was from M13 mGP1-2 (ATCC 40303). The sequence of M13 mGP1-2 is given in U.S. Pat. No. 4,795,699, FIG. 9-1 through FIG. 9-8. Single-stranded M13 mGP1-2 DNA was prepared by the method of Tabor et al., 262 *J. Biol. Chem.* 16212, 1987). The concentration was 1.2 mM in 20 mM Tris-HCl pH 7.5, 2 mM EDTA.

The $^{32}$P-labeled 167 nucleotide single-stranded DNA fragment was prepared using a modification of the "labeling reaction" of a DNA sequencing reaction (Tabor and Richardson (84 *Proc. Natl. Acad. Sci U.S.A.* 4767, 1987), as follows: The primer "GTCCGACTCTAAGATGTCAC" was annealed to single-stranded mGP1-2 DNA in a reaction mixture (100 μl) containing 40 mM Tris-HCl, pH 7.5, 10 mM MgCl$_2$, and 50 mM NaCl, 20 μg single-stranded mGP1-2 DNA, and 120 ng primer. The mixture was heated to 65° C. for 2 min, then cooled to room temperature (about 20° C.) over 30 min. 1 μl 100 mM dithiothreitol, 2 μl of 60 μM each dGTP, dTTP, and dCTP, and 10 μl of [α-$^{32}$P]dATP (100 μCi, 3000 Ci/mmol) were added. The reaction was started by the addition of 0.5 μg of Δ28 T7 DNA polymerase complexed with E. coli thioredoxin (Tabor and Richardson, 264 J. Biol. Chem. 6447, 1989) (20 units of SEQUENASE Version 2.0 T7 DNA Polymerase (USB, Cleveland, Ohio) or 20 units of Klenow fragment (USB) will also work), and reaction mixture was incubated at room temperature for 10 min. 10 μl of 3 mM 4dNTPs were added, and the reaction mixture was incubated at room temperature for an additional 20 min. The reaction mixture was then incubated at 65° C. for 10 min to inactivate the DNA polymerase. 20 units of the restriction enzyme XmnI (USB) was added, and the reaction mixture was incubated at 37° C. for 60 min. 150 μl of formamide, 5 μl 0.5M EDTA, and 2 μl 2% bromphenol blue were added, and the mixture was incubated at 100° C. for 3 min. immediately prior to loading onto a 6% polyacrylamide gel in 7M urea. The polyacrylamide gel contained a 1:30 acryamide:bisacrylamide ratio. The gel buffer was 100 mM Tris-borate, pH 8.9, 1 mM EDTA.

After electrophoresis at 500 V for 5 hr, the radioactive band corresponding to the 167 nucleotide fragment had migrated approximately half the distance down the 30 cm gel. The radioactive band was eluted from the gel in the presence of 5 μg tRNA, using an ISCO electroelution apparatus. (This concentration of tRNA does not interfere with the homologous pairing reaction.) Other elution techniques for eluting fragments from polyacrylamide gels will suffice. The eluted DNA was precipitated with ethanol. The precipitated DNA was resuspended in 10 mM Tris-HCl, pH 7.5, 1 mM EDTA at a concentration of 20 nM (expressed as moles of fragment); the specific activity was 6×10$^6$ cpm/pmole of fragment.

Each renaturation reaction (25 μl) contained 10,000 cpm of $^{32}$P-labeled 167-mer prepared as described above (1.0 fmole fragment; 6.7 nM in nucleotide, 2.2 ng/ml), 1.0 fmole M13 mGP1-2 single-stranded DNA molecules (400 nM nucleotide, 130 ng/ml), 40 mM Tris-HCl, pH 7.5, 10 mM MgCl$_2$, 5 mM dithiothreitol, and 50 mM NaCl. Where present, 2 μl containing 1 μg purified gene 2.5 protein (4 mg/ml in 20 mM KPO$_4$, pH 7.4, 0.1M dithiothreitol, 0.1M EDTA, and 50% glycerol) diluted to a concentration of 0.5 mg/ml in 10 mM Tris-HCl, pH 7.5, 10 mM 2-mercaptoethanol, 0.5 mg/ml bovine serum albumin was provided. The reactions were incubated at 37° C. for times ranging from 15 sec to 1 hr. The reactions were stopped by the addition of 10 μl of 70% glycerol, 1% sodium dodecyl sulfate, and 0.05% bromphenol blue, and placed on ice. The samples were loaded onto a 8% agarose gel in a buffer containing 100 mM Tris-borate, pH 8.3, 1 mM EDTA. Electrophoresis was for 6 hr at a voltage of 40 Volts (12.6 Volt/cm) at room temperature. After electrophoresis, the gel was dried under vacuum and autoradiographed for varying times using Kodak XAR film.

Experiments were carried out using a range of gene 2.5 protein concentrations from 0.03 μg to 4 μg gene 2.5 protein per 25 μl reaction. In the absence of gene 2.5 protein, after a 1 hr incubation at 37° C., <0.5% of the radioactively-labeled fragments were annealed to the M13 DNA (giving an estimated half time for renaturation greater than about 3 weeks). Stimulation of renaturation of the radioactively-labeled fragment to M13 DNA could be detected at all concentrations of gene 2.5 protein used. Maximum stimulation occurred using 1 μg/ml to 2 μg/ml of gene 2.5 protein. Under these conditions, over 25% of the radioactively labeled fragments were annealed to the M13 DNA within 30 sec. (estimated half time for renaturation of about 1 minute). Thus, the stimulation is at least approximately 50×120=6000 fold, but probably at least 30,000 fold.

When this experiment (using the conditions outlined above with about 2μg of the indicated binding protein in the reaction mix in place of gene 2.5 protein) were carried out with T4 phage-gene 32 protein (from U.S.B.), after a 60 min incubation approximately 1% of the radioactively labeled fragments had annealed. Thus, the stimulation with gene 32 protein is less effective than with gene 2.5 protein by a factor of approximately 25×120 =3000. With recA protein (from U.S.B.) little renaturation was observed in the absence of ATP, and even in the presence of about 500 μM ATP the rate was still 60 fold slower than with gene 2.5 protein. These data are shown in Table II. E. coli SSB protein (U.S.B.) did not significantly enhance renaturation of these single-stranded DNA molecules. Similar relative rates are obtained in the presence of an excess of heterologous DNA, e.g., calf thymus or salmon sperm DNA (single-stranded, ten fold or even greater excess).

TABLE II

| Rate of Renaturation of 167 base fragment to M13 DNA | |
|---|---|
| Protein | $t_{1/2}$ (min) |
| None | >30,000 (3 weeks) |
| +E. coli SSB protein | >30,000 (3 weeks) |
| +T4 gene 32 protein | 3,000 (2 days) |
| +E. coli recA protein (+ATP) | 60 |
| +T7 gene 2.5 protein | 1 |

Use

As is evident from the experiments described above, gene 2.5 protein or its equivalent can be used in hybridization reactions performed even at low nucleic acid concentrations in the presence of heterologous DNA. Thus, the testing of stool, blood, urine, or sputum samples for the presence of a low concentration of virus or bacteria, or even for the presence of a genetic defect in a cell, can be performed without the need for any significant amount of amplification of the nucleic acid, either by growing the organism or cell, or by genetic amplification, e.g., polymerase chain reaction. The method of this invention thus requires performing a hybridization reaction using any desired methodology but including a gene 2.5 protein, or its functional equivalent. Given that even nucleic acid as low as 2 ng/ml can be caused to hybridize within seconds, this provides an extremely sensitive method for assay of specific hybridization. The detection system useful in such hybridization includes radioactive labels or non-radioactive labels, for example, use of digoxigenin-labelled nucleic acid probes as described by Holke et al., 12 BioTechniques 104, 1992, hereby incorporated by reference herein.

Other embodiments are within the following claims.

We claim:

1. A method for hybridization of nucleic acids to detect the presence of a nucleic acid sequence in a sample comprising a population of different nucleic acid sequences using a nucleic acid probe, wherein said nucleic acid probe hybridizes under hybridizing conditions with said nucleic acid sequence but does not hybridize to said different nucleic acid sequences in said population under said conditions, comprising the steps of:

contacting a sample comprising the population of different nucleic acid sequences, and potentially comprising the presence of said nucleic acid sequence, with said nucleic acid probe under hybridizing conditions in the presence of a T-7 type single stranded DNA binding protein which in the absence of nucleoside triphosphates stimulates greater than 500 fold the renaturation of an M13mGP1-2 single stranded DNA molecule with 1.0 fmole of a 167mer fragment generated from the primer, SEQ ID NO:1, and an M13mGP1-2 template, and detecting hybridization of said probe with said nucleic acid sequence whereby the presence of said nucleic acid sequence in said sample.

2. The method of claim 1, wherein said population of nucleic acid sequences and said nucleic acid probe comprise heterologous DNA.

3. The method of claim 1, wherein said protein is T7 gene 2.5 protein.

4. The method of claim 3, wherein said protein is produced by recombinant DNA technology.

5. The method of claim 1, wherein said method is a solution phase hybridization.

6. The method of claim 1, wherein said method is a Southern or a northern blot.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 20
( B ) TYPE: NUCLEIC ACID
( C ) STRANDEDNESS: Single
( D ) TOPOLOGY: Linear ( x i ) SEQUENCE DESCRIPTION: SEQ ID NO: 1:

GTCCGACTCT AAGATGTCAC    20